United States Patent
Wang

(10) Patent No.: US 8,765,057 B2
(45) Date of Patent: Jul. 1, 2014

(54) AUTOMATIC DETECTION INSTRUMENT FOR STOOL SPECIMEN

(75) Inventor: Zhong Wang, Shanghai (CN)

(73) Assignee: Jihong Biotech (Shanghai) Co., Ltd., Yang Pu District, Shanghai (CN)

( * ) Notice: Subject to any disclaimer, the term of this patent is extended or adjusted under 35 U.S.C. 154(b) by 382 days.

(21) Appl. No.: 13/202,398

(22) PCT Filed: Feb. 9, 2010

(86) PCT No.: PCT/CN2010/070581
§ 371 (c)(1),
(2), (4) Date: Oct. 22, 2011

(87) PCT Pub. No.: WO2010/094228
PCT Pub. Date: Aug. 26, 2010

(65) Prior Publication Data
US 2012/0051974 A1 Mar. 1, 2012

(30) Foreign Application Priority Data
Feb. 19, 2009 (CN) .......................... 2009 1 0046365

(51) Int. Cl.
*G01N 21/00* (2006.01)
*G01N 15/04* (2006.01)
*G01N 33/00* (2006.01)
*G01N 15/10* (2006.01)
*G01N 33/48* (2006.01)

(52) U.S. Cl.
USPC .............................. 422/67; 422/68.1; 422/73

(58) Field of Classification Search
USPC .......................................................... 422/67
See application file for complete search history.

(56) References Cited

U.S. PATENT DOCUMENTS

| | | | | |
|---|---|---|---|---|
| 5,665,312 | A * | 9/1997 | Sperber et al. | 422/81 |
| 5,939,326 | A * | 8/1999 | Chupp et al. | 436/43 |
| 6,812,032 | B1 * | 11/2004 | Carver et al. | 436/63 |
| 6,943,029 | B2 * | 9/2005 | Copeland et al. | 436/46 |
| 2002/0098117 | A1 * | 7/2002 | Ammann et al. | 422/64 |
| 2005/0095724 | A1 * | 5/2005 | Shibutani et al. | 436/180 |
| 2005/0281707 | A1 * | 12/2005 | Nakaya et al. | 422/63 |
| 2007/0048868 | A1 * | 3/2007 | Shibata et al. | 436/43 |
| 2008/0026472 | A1 * | 1/2008 | Haack et al. | 436/48 |

FOREIGN PATENT DOCUMENTS

WO PCT/CN2010/070581 5/2010

* cited by examiner

*Primary Examiner* — Jill Warden
*Assistant Examiner* — Brittany Fisher
(74) *Attorney, Agent, or Firm* — Global IP Services; Tianhua Gu

(57) ABSTRACT

The invention discloses an automatic detection instrument for stool specimen, comprising an automatic controller; a dilution device used for adding quantitative diluent into the stool specimen; a stirring and blending device used for stirring and blending the diluted stool specimen; a detecting unit used for detecting the stool specimen, and an aspirating and cleaning device connected with the detecting unit through pipelines and used for transmitting the stool specimen to the detecting unit and cleaning the detecting unit and the connecting pipelines after detection. The detection instrument of the invention can automatically carry out quantitative dilution, physical microscopic examination and partial chemical detection for specimen completely in comparatively sealed pipelines, thereby reducing the link of air contact, reducing the contamination for the environment and laboratory, and improving the work efficiency by using computer software for automatic control.

17 Claims, 4 Drawing Sheets

AUTOMATIC DETECTION INSTRUMENT FOR STOOL SPECIMEN

CROSS REFERENCE TO RELATED PATENT APPLICATION

The present application is the US national stage of PCT/CN2010/070581 filed on Feb. 9, 2010, which claims the priority of the Chinese patent application No. 200910046365.7 filed on Feb. 19, 2009, which application is incorporated herein by reference.

FIELD OF THE INVENTION

The invention relates to a medical detecting device, particularly to an automatic detection instrument for stool specimen.

BACKGROUND OF THE INVENTION

The existing methods employed for the detection of stool specimen, such as stool routine detection and partial chemical detection of stool specimen are relatively backward. The disadvantages of the above methods are as follows: 1) All the links, for example, from the collection of specimen to the operation and examination of specimen, and the final specimen waste liquid treatment may result in contamination for the environment and laboratory; 2) in order to prevent the spread of infectious diseases, cotton swabs used for collecting the specimen of the patient and containers for holding the specimen of the patient must be subject to special treatment; the more the treatment links are, the higher the chance of contamination is; moreover, it is very insanitary during the examination and operation process; 3) there is no uniform and standard report format.

SUMMARY OF THE INVENTION

The technical problem to be solved by the invention is to provide a detection instrument capable of automatically performing quantitative dilution and detection for stool specimen and automatically cleaning after detection to avoid contamination.

To solve the above technical problem, the invention adopts the following technical solution: an automatic detection instrument for stool specimen, comprising the following parts: an automatic controller; a dilution device used for adding quantitative diluent into the stool specimen; a stirring and blending device used for stirring and blending the diluted stool specimen; a detecting unit used for detecting the stool specimen; an aspirating and cleaning device connected with the detecting unit through pipelines and used for transmitting the stool specimen to the detecting unit and cleaning the detecting unit and the connecting pipelines after detection.

Moreover, detecting unit comprises a physical detecting sub-unit and a chemical detecting sub-unit.

More preferably, the physical detecting sub-unit comprises microscope, microscope camera mounted on the microscope, and counting chamber positioned on the stage of the microscope; the counting chamber is connected with the aspirating and cleaning device through pipelines.

Moreover, the aspirating and cleaning device comprises—a sample aspirating needle, a diluent intake, and an aspirating peristaltic pump connected between the sample aspirating needle and the diluent intake; the counting chamber is connected between the sample aspirating needle and the aspirating peristaltic pump.

Moreover, both ends of the counting chamber are provided with an electromagnetic pinch-off valve respectively.

Moreover, a sample adding needle is fixed on a first lifting frame which is driven by a first motor.

Moreover, the dilution device comprises a sample injector communicated with the diluent intake; the sample injector is communicated with the sample aspirating needle via a one-way valve.

Preferably, the sample injector is a syringe typed sample injector.

Moreover, the sample injector is connected to a second lifting frame which is driven by a second motor.

Preferably, the chemical detecting sub-unit comprises a chemical detecting chamber, and the chemical detecting chamber is also connected between the sample aspirating needle and the aspirating peristaltic pump.

Preferably, the chemical detecting sub-unit comprises a chemical detecting chamber, wherein an end of the chemical detecting chambers connected with the counting chamber, the other end is connected with a waste liquid peristaltic pump, and the waste liquid peristaltic pump is connected with a waste liquid aspirating needle.

Preferably, an electromagnetic pinch-off valve is arranged between the chemical detecting chamber and the counting chamber.

Preferably, a specimen box holder is arranged below the first lifting frame.

Moreover, the detection instrument further comprises a video camera opposite to the side surface of the specimen box holder.

Moreover, a specimen box identification photoelectric sensor arranged above the video camera.

Moreover, the specimen box holder is mounted on a linear guide track which is driven by a step motor.

Moreover, said specimen box holder further comprises a specimen box inside.

Moreover, said stirring and blending device comprises a stirring motor and a rotatable sampling spoon, and the sampling spoon is positioned in the specimen box; when the first lifting frame descends, the sample adding needle is inserted into the specimen box, and the stirring motor is connected with the sampling spoon coaxially.

Preferably, the detection instrument further comprises a display which is connected with the automatic controller.

The automatic controller in the invention can control the dilution device to perform quantitative dilution for the stool specimen automatically, control the stirring and blending device to blend the specimen, and control the aspirating and cleaning device to transmit the specimen to the detecting unit for detection through pipelines, and clean the detecting unit and the connecting pipelines after detection. The whole process is carried out in comparatively sealed pipelines completely, thereby reducing the link of exterior contact, reducing the contamination for the environment and laboratory, and improving the work efficiency by using computer for automatic control.

Figure 1:
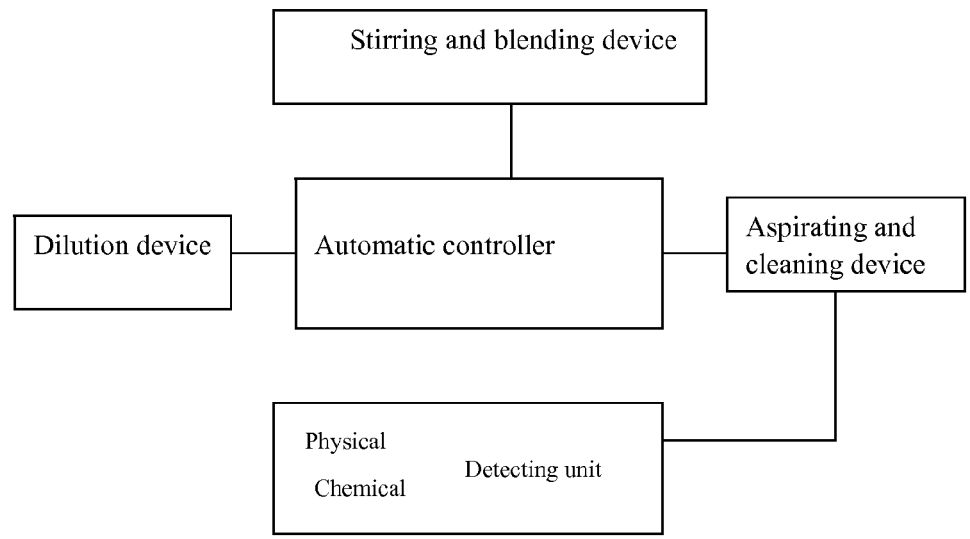
FIG. 1 is a composition schematic drawing of functional modules of the automatic detection instrument for stool specimen according to the invention.

Drawing reference signs are as follows:
11. sample injector
12. diluent intake
13. specimen box
14. counting chamber
15. chemical detecting chamber
16. sample aspirating needle
17. waste liquid aspirating needle
18. sample aspirating peristaltic pump
19. waste liquid peristaltic pump
21. first pipeline tee
22. second pipeline tee
23. third pipeline tee
24. tee-pipeline electromagnetic pinch-off valve
32. one-way valve
33. first electromagnetic pinch-off valve
34. second electromagnetic pinch-off valve
35. third electromagnetic pinch-off valve
41. first lifting frame
42. second lifting frame
43. linear guide track
44. regularly-shaped rotating joint
51. first motor
52. second motor
53. step motor
54. stirring motor
61. specimen box holder
62. specimen box identification photoelectric sensor
63. video camera
7. display
8. microscope
81. microscope camera
82. microscope stage
131. box cover
132. open hole
133. rotating shaft
134. sampling spoon
135. filter screen
136. buffer chamber

DETAILED DESCRIPTION OF THE EMBODIMENTS

The invention is described below with reference to accompanying drawings in details.

Firstly as shown in FIG. 1, the automatic detection instrument for stool specimen according to the invention comprises an automatic controller, a dilution device, a stirring and blending device, a detecting unit and an aspirating and cleaning device, wherein the dilution device is capable of adding quantitative diluent into the stool specimen under the control of the automatic controller; and the stirring and blending device is capable of stirring and blending the diluted stool specimen under the control of the automatic controller; and the detecting unit is used for detecting the stool specimen; and the aspirating and cleaning device is connected with the detecting unit through pipelines and is capable of, under the control of the automatic controller, transmitting the stool specimen to the detecting unit and automatically cleaning the detecting unit and the connecting pipelines after detection, in order to facilitate the next detection. The detecting unit may comprise a physical detecting sub-unit and a chemical detecting sub-unit, the automatic controller may be a computer.

Figure 2:
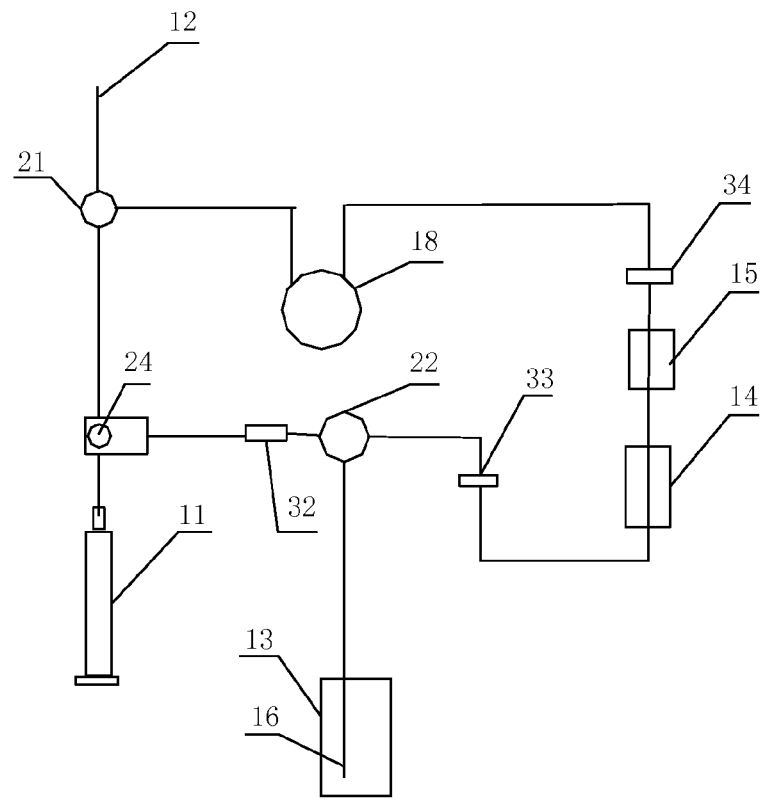
FIG. 2 is a pipeline connection schematic drawing according to an embodiment of the invention.

As shown in FIG. 2, the collected stool specimen is put into a specimen box 13, a sample aspirating needle 16 is inserted into the specimen box 13, and a sample injector 11 is connected with a diluent intake 12 through pipelines. A tee-pipeline electromagnetic pinch-off valve 24 and a first pipeline tee 21 are arranged between the sample injector 11 and the diluent intake 12, while the sample aspirating needle 16 is connected with the tee-pipeline electromagnetic pinch-off valve 24 via a second pipeline tee 22 and a one-way valve 32. When the tee-pipeline electromagnetic pinch-off valve 24 is communicated with the sample injector 11 and the diluent intake 12, simultaneously the pipelines between the sample injector 11 and the sample aspirating needle 16 are disconnected, the sample injector 11 may aspirate quantitative amount of diluent from the diluent intake 12, then the tee-pipeline electromagnetic pinch-off valve 24 switches actions, so that the pipelines between the sample injector 11 and the diluent intake 12 are disconnected, at the same time the pipelines between the sample injector 11 and the sample aspirating needle 16 are connected, then the sample injector 11 is pressed, and the diluent is injected into the specimen box 13 via the one-way valve 32 and the sample aspirating needle 16, such that the quantitative dilution of the stool specimen is finished. The above diluent intake 12, the tee-pipeline electromagnetic pinch-off valve 24, the sample injector 11, the one-way valve 32, the sample aspirating needle 16 and the connecting pipelines thereof constitute the diluent device.

One end of a sample aspirating peristaltic pump 18 is communicated with the diluent intake 12 via the first pipeline tee 21, the other end is connected with the sample aspirating needle 16 through the pipelines and the second pipeline tee 22 so as to constitute the aspirating and cleaning device. The counting chamber 14 of the physical detecting sub-unit and the chemical detecting chamber 15 of the chemical detecting sub-unit are connected in series between the sample aspirating needle 16 and the sample aspirating peristaltic pump 18. When the sample aspirating peristaltic pump 18 rotates positively, the specimen liquid is aspirated out from the specimen box 13 by the sample aspirating needle 16, and enters the counting chamber 14 and the chemical detecting chamber 15 to facilitate physical and chemical detection. Both ends of the counting chamber 14 are provided with a first electromagnetic pinch-off valve 33, and a second electromagnetic pinch-off valve 34, respectively, and when the valves are closed, the specimen liquid inside the counting chamber can be made stable as soon as possible, in order to facilitate observation and counting under microscope; meanwhile, when the counting chamber is back flushed, the first and the second electromagnetic pinch-off valves 33, 34 are opened and closed repeatedly, so that the pressure inside the pipelines can be increased, and the flushing effect can be improved. After the detection is finished, the sample aspirating peristaltic pump 18 rotates reversibly, and the diluent enters along the pipelines to clean the counting chamber 14, the chemical detecting chamber 15 and the sample aspirating needle 16, and the cleaning waste liquid flows into the specimen box 13 through the sample aspirating needle 16 to be treated collectively. Due to the action of the one-way valve 32, the waste liquid can be avoided from entering the dilution pipelines and causing contamination.

Figure 3:
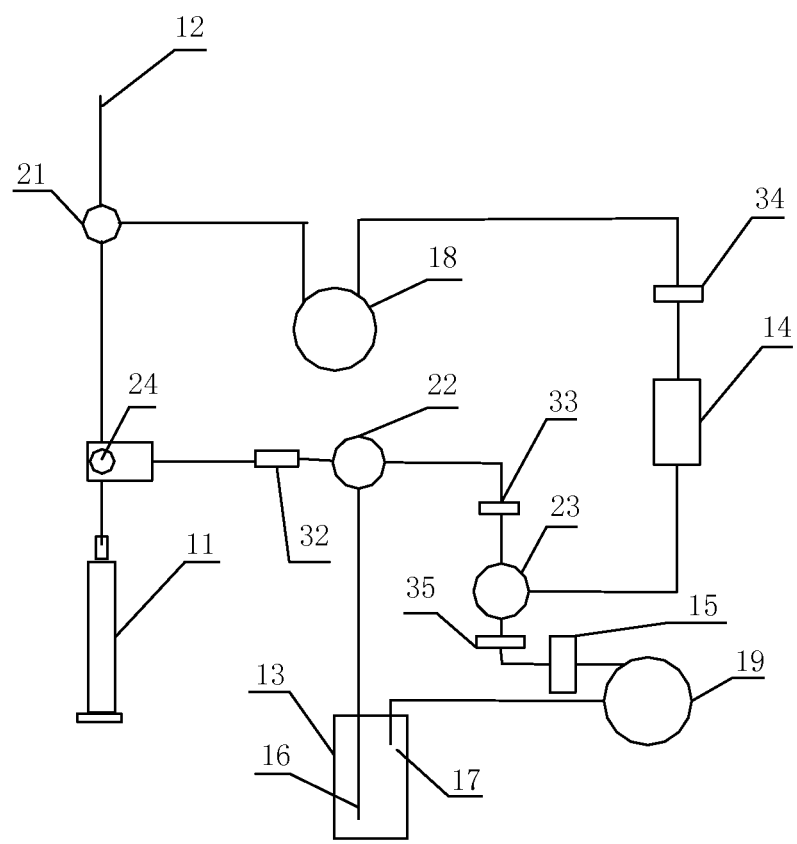
FIG. 3 is a pipeline connection schematic drawing according to another embodiment of the invention.

FIG. 3 is another embodiment of the invention. Different from the FIG. 2, the chemical detecting chamber 15 is not connected to the aspirating and cleaning pipelines in series with the counting chamber 14. One end of the chemical detecting chamber 15 is connected with the counting chamber 14 via a third electromagnetic pinch-off valve 35 and a third pipeline tee 23, the other end is connected with a waste liquid peristaltic pump 19, and the waste liquid peristaltic pump 19 is connected with a waste liquid aspirating needle 17, and the waste liquid aspirating needle 17 is also inserted into the specimen box 13. When the third electromagnetic pinch-off valve 35 is closed, the specimen liquid only enters the counting chamber 14 for the physical detection. If the chemical detection is needed, under the condition that the first electromagnetic pinch-off valve 33 is closed and the second and the third electromagnetic pinch-off valves 34, 35 are opened, the sample aspirating peristaltic pump 18 and the waste liquid peristaltic pump 19 are opened to transmit the specimen liquid into the chemical detecting chamber 15 for chemical detection. The chemical detecting chamber 15 can be provided with a test strip in a casing, and the specimen is automatically fed to the test strip. After the detection is finished, the sample aspirating peristaltic pump 18 and the waste liquid peristaltic pump 19 are continued to be opened, the counting chamber 14 and the chemical detecting chamber 15 are cleaned by diluent, and the waste liquid enters the specimen box 13 through the waste liquid aspirating needle 17, then the first electromagnetic pinch-off valve 33 is opened to clean the sample aspirating needle 16. If the sample aspirating peristaltic pump 18 rotates positively, the function of aspirating the specimen into the counting chamber 14 can be completed, and if the sample aspirating peristaltic pump 18 rotates reversibly, the cleaning of the counting chamber 14, the chemical detecting chamber 15, and the pipelines can be completed, and the operation time and speed of rotation of the sample aspirating peristaltic pump 18 are adjustable.

Figure 6:
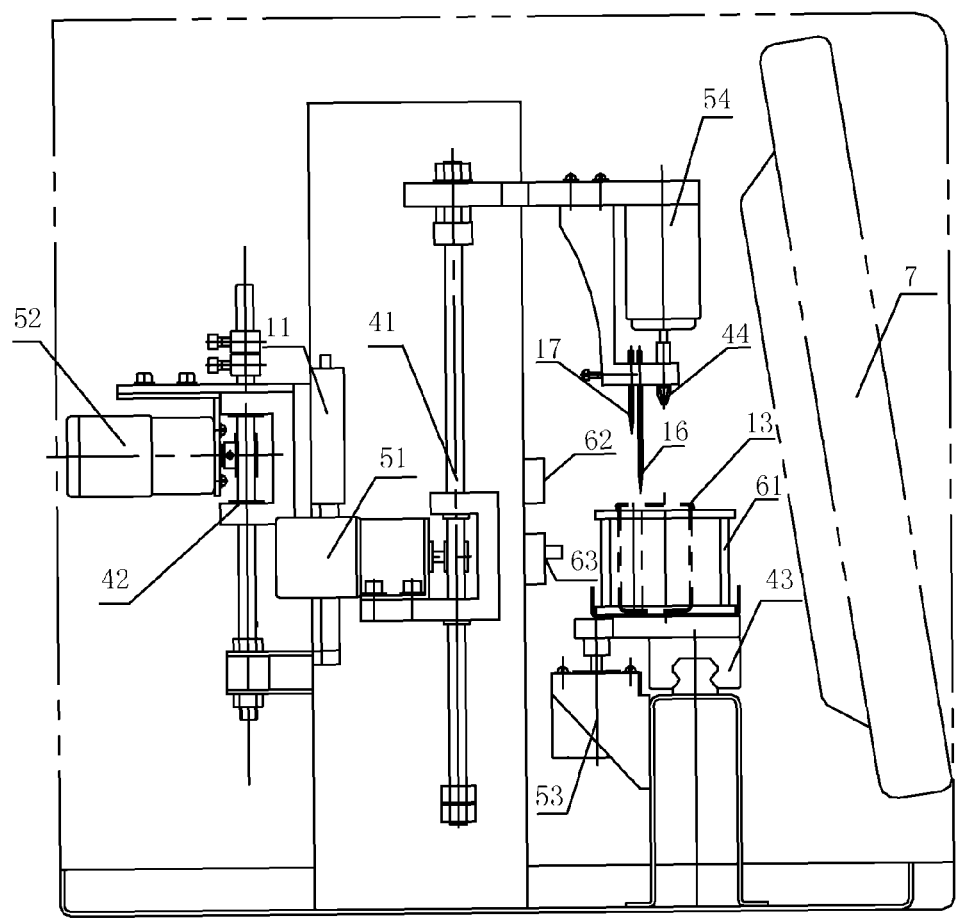
FIG. 6 is a structural schematic drawing of a specimen box.

As shown in FIG. 6, the specimen box 13 can be provided with a box cover 131, the box cover 131 is provided with an open hole 132 in order to facilitate the insertion of the sample aspirating needle 16 and the waste liquid aspirating needle 17. The box cover 131 is also provided with a rotating shaft 133, and the rotating shaft 133 can rotate freely relative to the box cover. The upper end of the rotating shaft 133 may be connected with a motor, and the lower end is connected with a sampling spoon 134, which can be used for collecting the stool specimen, and after the specimen is put into the specimen box and diluent is added, the sampling spoon 134 can then play the role of stirring and blending, when the motor drives the rotating shaft 133 to rotate. The specimen box 13 is provided with a filter screen 135, the filter screen 135 isolates the space inside the box into an upper cavity and a lower cavity, wherein the lower cavity is the buffer room 136, and the sample aspirating needle 16 can be inserted into the buffer room 136 to aspirate filtered specimen liquid.

Figure 4:
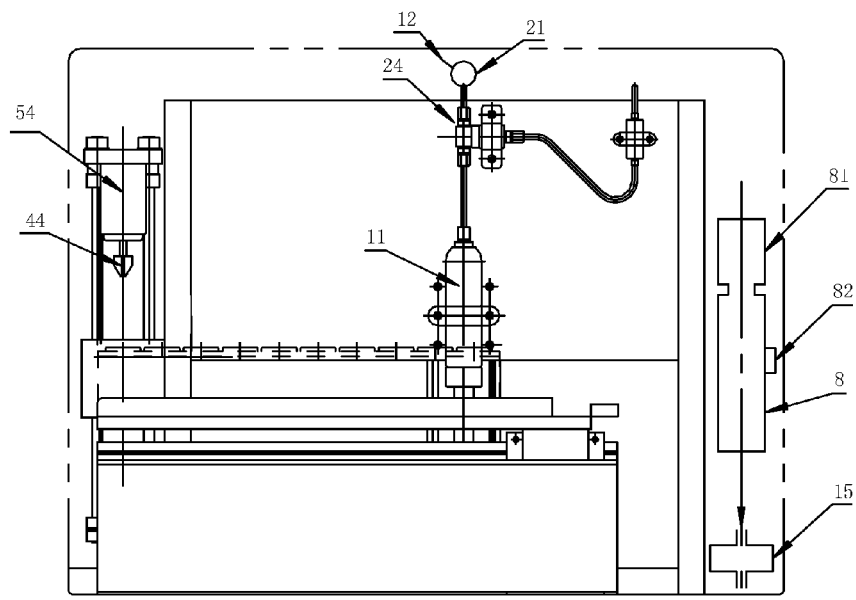
FIG. 4 is a structural schematic drawing of the invention (in the front view direction).
Figure 5:
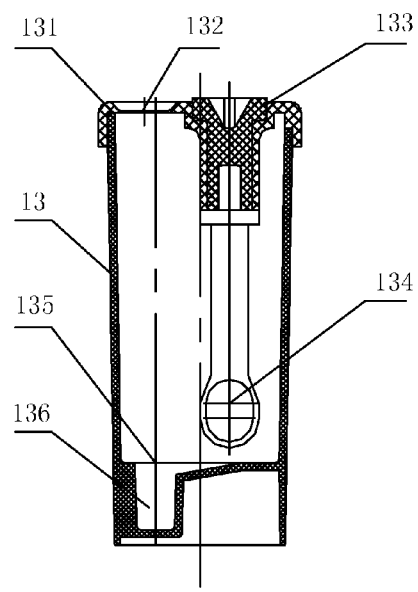
FIG. 5 is a structural schematic drawing of the invention (in the left view direction).

As shown in FIG. 4 and FIG. 5, the invention further comprises a first lifting frame 41. The sample aspirating needle 16, the waste liquid aspirating needle 17 and a regularly-shaped rotating joint 44 are all mounted on the first lifting frame 41, and the regularly-shaped rotating joint 44 is connected with a stirring motor 54. The first lifting frame 41 is driven by a first motor 51, for driving the regularly-shaped rotating joint 44, the sample aspirating needle 16 and the waste liquid aspirating needle 17 to rise and fall, wherein one function is to make the sample aspirating needle 16 and the waste liquid aspirating needle 17 be inserted into the specimen box 13 and enter the designed working position, the second function is to make the regularly-shaped rotating joint 44 be engaged with the rotating shaft on the specimen box cover, so that the stirring motor 54 drives the sampling spoon 134 to rotate to perform stirring and blending. The stirring motor 54 and the sampling spoon 134 thus constitute the stirring and blending device.

A syringe typed sample injector is employed as the sample injector 11. The pintle of the sample injector 11 is connected to the second lifting frame 42, and the second lifting frame 42 drives the pintle to be pulled out and pushed in so as to aspirate and discharge the diluent. The second lifting frame 42 is driven by a second motor 52. The second motor 52 operates to set positions under the control of the photoelectric sensor.

The specimen box 13 is placed on the specimen box holder 61, and the specimen box holder 61 serves as the test tube rack positioned below the first lifting frame 41 for holding a plurality of specimen boxes. The specimen box holder 61 is placed on a linear guide track 43, and the linear guide track 43 is driven by a step motor 53. The linear guide track 43 fixes and drives the specimen box holder 61 to operate, and there are strict requirements on the operation frequency and distance of each operation, and the operation is controlled according to programs, and the location is validated by the photoelectric sensor.

A video camera 63 is mounted near the specimen box holder 61 and opposite to the side surface of the specimen box holder 61, and connected with the automatic controller (computer) for observing the diluting and stirring working status of the specimen, and observing the shape and color of the specimen simultaneously. A specimen box identification photoelectric sensor 62 is arranged above the video camera 63 and faces the position of the specimen box cover for identifying the specimen box. When the linear guide track 43 drives the specimen box holder 61 to operate, the specimen box identification photoelectric sensor 62 works to scan the existence or absence of specimen box on the specimen box holder 61, the number of the specimen boxes, and the position of the specimen box on the specimen box holder 61. The instrument performs operation automatically according to the scanning data provided by the specimen box identification photoelectric sensor 62. If the specimen box identification photoelectric sensor 62 does not receive the signal of the specimen box, the next detection operation is not needed to be performed.

A display 7 is connected with the automatic controller (computer) to be capable of performing program operation and displaying the video signal acquired by the video camera 63.

The physical detecting sub-unit comprises a microscope 8, a microscope camera 81 mounted on the microscope, and a counting chamber 14 positioned on the microscope stage 82 of the microscope for observing and counting by using the microscope, and the image acquired by the microscope camera 81 is also displayed on the display 7.

When the invention is used, the main power is firstly connected, the specimen box 13 is placed on the specimen box holder 61, then the specimen box holder 61 is pushed into the instrument from the specimen box holder window, and a switch is triggered, such that the step motor 53 rotates positively to drive the linear guide track 43 to operate along the positive direction, and then operate along the reverse direction after the positive direction operation reaches the end of the positive rotation. At this moment, the specimen box identification photoelectric sensor 62 works to detect the existence or absence of the specimen box 13 on the specimen box holder 61; if the specimen box 13 is not detected, an informing dialog box appears to prompt to put in the specimen box 13, and if the specimen box 13 is detected, the next operation is continued to be performed. The linear guide track 43 stops at a position at which the first specimen box on the specimen box holder 61 is aligned with the sample aspirating needle 16, the waste liquid aspirating needle 17 and the regularly-shaped rotating joint 44 on the above first lifting frame 41. Now, observation can be performed according to the color comparison on the software, and the video camera 63 is opened for observing the operation status of the instrument, for example, whether the regularly-shaped rotating joint 44 is aligned with the interface on the specimen box cover.

The first motor 51 rotates positively to drive the first lifting frame 41 to operate downwards, meanwhile the stirring motor 54 rotates at a slow speed, the first lifting frame 41 drives the sample aspirating needle 16, the waste liquid aspirating needle 17 and the regularly-shaped rotating joint 44 to be inserted into the designed position of the specimen box 13. The sample aspirating needle 16 enters the buffer chamber after passing through the filter screen of the specimen box 13. Meanwhile, the regularly-shaped rotating joint 44 is meshed with the rotating shaft of the specimen box. The second motor 52 rotates positively to drive the second lifting frame 42 to operate downwards, pull out the pintle of the syringe typed sample injector 11 and suck the diluent. This process is a process of aspirating diluent by the sample injector 11.

In combination with FIG. 3, the tee-pipeline electromagnetic pinch-off valve 24 then switches to the inner passage, the second motor 52 rotates reversibly, the second lifting frame 42 operates upwards, and the diluent is added into the specimen box 13 by the one-way valve 32, the second pipeline tee 22 and the sample aspirating needle 16, so that the process of filling the pipeline with diluent is completed. This process is a process of adding diluent into the specimen box.

The stirring motor 54 then drives the regularly-shaped rotating joint 44 to rotate along the positive and reverse directions at the designed speed, and drives the sampling spoon inside the test tube to rotate in order to complete the designed rotation time, and the blending of specimen inside the specimen box 13 is thereby realized.

The sample aspirating peristaltic pump 18 then rotates positively, and the diluted and blended specimen is pumped into the counting chamber 14 through the sample aspirating needle 16, the second pipeline tee 22, and the third pipeline tee 23. The aspirated specimen liquid stops at the following second electromagnetic pinch-off valve 34. After the sample aspiration is finished, the first electromagnetic pinch-off valve 33 and the second electromagnetic pinch-off valve 34 at both ends of the counting chamber 14 are closed to close the silica gel pipelines, and the sample inside the counting chamber 14 is made still quickly to facilitate observation by the microscope. The connecting pipelines between the counting chamber 14 and the sample aspirating peristaltic pump 18 is long enough, so that the specimen will not be aspirated into the diluent via the sample aspirating peristaltic pump 18. The above process is a process of sent the diluted and blended specimen liquid into the counting chamber 14 for detection.

At this moment, the stirring motor 54 stops operating. The software then displays the prompt to open the microscopic examination, after the operator clicks the button, the microscope inside the instrument starts working. The microscope camera sends the microscopic examination image to the display of the computer, and after one field is observed and the result is recorded, the operator can perform operation based on software button, and click on the 'manual sample add on' button. The sample aspirating peristaltic pump 18 rotates positively, and the first electromagnetic pinch-off valve 33 and the second electromagnetic pinch-off valve 34 are opened, and a small amount of specimen liquid is aspirated. The operation continues for only one second, then the sample aspirating peristaltic pump 18 stops operating, the first electromagnetic pinch-off valve 33 and the second electromagnetic pinch-off valve 34 are closed again, the pipelines are occluded, and the operator records the microscopic examination result again. The above process can be performed for four times at most, and the operator can control the movement of the stage of the microscope to achieve the purpose of converting fields. The above is the microscopic examination process of the specimen liquid.

After the microscopic examination is completed, if some necessary chemical detections, such as occult blood are required to be performed for the patient specimen on the laboratory sheet, then chemical detection should be performed for the specimen liquid. The operator clicks the 'chemical detection' button of the software. Then the second electromagnetic pinch-off valve 34 is opened, the first electromagnetic pinch-off valve 33 is closed, and the sample aspirating peristaltic pump 18 rotates reversibly, and the specimen liquid is sent into the chemical detecting chamber 15 finally after passing through the counting chamber 14 and the third pipeline tee 23. The operator now adds the test strip template at the test strip template adding window of the front panel of the instrument, and clicks the 'chemical detection' button again, then the sample aspirating peristaltic pump 18 rotates reversibly, and the specimen liquid is added to the test strip template, and the template is then taken out for waiting for the observation result. This operation can be performed for four times.

After the operator presses the 'print' key upon the completion of microscopic examination and chemical detection, the instrument enters the cleaning process. The chemical detecting pipelines are firstly cleaned, and the sample aspirating peristaltic pump 18 rotates reversibly, and the diluent cleans the first pipeline tee 21, the sample aspirating peristaltic pump 18, the counting chamber 14, the third pipeline tee 23 and the chemical detecting chamber 15 by passing therethrough, meanwhile the waste liquid peristaltic pump 19 rotates positively, and the waste liquid is discharged into the specimen box 13 via the chemical detecting chamber 15, the waste liquid peristaltic pump 19 and the waste liquid aspirating needle 17.

After the cleaning process is finished, the waste liquid peristaltic pump 19 stops working, the sample aspirating peristaltic pump 18 rotates positively, and the diluent inside the chemical detecting chamber 15 and the third pipeline tee 23 is drained, then the third electromagnetic pinch-off valve 35 is closed, and the pipelines are closed, the sample aspirating peristaltic pump 18 rotates reversibly, and the diluent is discharged into the specimen box 13 via the first pipeline tee 21, the sample aspirating peristaltic pump 18, the counting chamber 14, the third pipeline tee 23, the second pipeline tee 22 and the sample aspirating needle 16, and meanwhile the counting chamber 14 is cleaned. During the process, if an abnormal operation occurs, an alarm dialog box automatically appears. During the process, the first and the second electromagnetic pinch-off valves 33, 34 alternate one second of work with half a second of stop, and the opening and closing are repeatedly performed. By the method, the pressure inside the cleaned pipelines is increased, and the cleaning effect is improved.

The above process is a process of detecting a specimen box and cleaning the instrument.

After the cleaning process is finished, the first lifting frame 41 operates upwards. After the first lifting frame 41 is in place, the syringe typed sample injector 11 aspirates diluent again, and the position of the next specimen box is located by the linear guide track 43 according to the signal input by the specimen box identification photoelectric sensor 62, and the same operation is performed for the next specimen. After all the specimen operations for a specimen box holder 61 are finished, the instrument transmits the specimen box holder 61 to the designed position, enters the standby status, and prints the detection report.

If there is no chemical detection item to be performed on the laboratory sheet, the operator can press the 'print' key after the microscopic examination recording is completed, the instrument then enters the cleaning process for the counting chamber 14, and the subsequent operations are the same.

The operation, operation time and operation direction of the motor in the invention are all controlled by software, and all the circuit principles are the known technologies.

All literatures described herein are hereby incorporated by reference in their entirety. It should also be understood that, one skilled in the art can make various modifications or changes to the present invention after reading the above disclosures of the present invention, and these equivalent forms are still in the scope limited by the attached claims of this application.

What is claimed is:

1. An automatic detection instrument for stool specimen comprising the following parts:
    an automatic controller;
    a dilution device used for adding quantitative diluent into the stool specimen;
    a stirring and blending device used for stirring and blending the diluted stool specimen;
    a detecting unit used for detecting the stool specimen including a physical detecting sub-unit and a chemical detecting sub-unit, the physical detecting sub-unit comprises a microscope, a microscope camera mounted on the microscope, and a counting chamber positioned on the stage of the microscope, the counting chamber is connected with the aspirating and cleaning device through pipelines;
    an aspirating and cleaning device connected with the detecting unit through pipelines and used for transmitting the stool specimen to the detecting unit and cleaning the detecting unit and the connecting pipelines after detection.

2. The automatic detection instrument for stool specimen according to claim 1, wherein the aspirating and cleaning device comprises a sample aspirating needle, a diluent intake, and a sample aspirating peristaltic pump connected between the sample aspirating needle and the diluent intake; the counting chamber is connected between the sample aspirating needle and the sample aspirating peristaltic pump.

3. The automatic detection instrument for stool specimen according to claim 2, wherein both ends of the counting chamber are provided with an electromagnetic pinch-off valve, respectively.

4. The automatic detection instrument for stool specimen according to claim 2, wherein a sample adding needle is fixed on a first lifting frame which is driven by a first motor.

5. The automatic detection instrument for stool specimen according to claim 2, wherein the dilution device comprises a sample injector communicated with the diluent intake; the sample injector is communicated with the sample aspirating needle via a one-way valve.

6. The automatic detection instrument for stool specimen according to claim 5, wherein the sample injector is a syringe typed sample injector.

7. The automatic detection instrument for stool specimen according to claim 6, wherein the sample injector is connected to a second lifting frame which is driven by a second motor.

8. The automatic detection instrument for stool specimen according to claim 2, wherein the chemical detecting sub-unit comprises a chemical detecting chamber, and the chemical detecting chamber is also connected between the sample aspirating needle and the sample aspirating peristaltic pump.

9. The automatic detection instrument for stool specimen according to claim 2, wherein the chemical detecting sub-unit comprises a chemical detecting chamber, an end of the chemical detecting chamber is connected with the counting chamber, the other end is connected with a waste liquid peristaltic pump, and the waste liquid peristaltic pump is connected with a waste liquid aspirating needle.

10. The automatic detection instrument for stool specimen according to claim 9, wherein an electromagnetic pinch-off valve is arranged between the chemical detecting chamber and the counting chamber.

11. The automatic detection instrument for stool specimen according to claim 4, wherein a specimen box holder is arranged below the first lifting frame.

12. The automatic detection instrument for stool specimen according to claim 11, further comprising a video camera opposite to the side surface of the specimen box holder.

13. The automatic detection instrument for stool specimen according to claim 12, wherein a specimen box identification photoelectric sensor is arranged above the video camera.

14. The automatic detection instrument for stool specimen according to claim 11, wherein the specimen box holder is mounted on a linear guide track which is driven by a step motor.

15. The automatic detection instrument for stool specimen according to claim 11, wherein the specimen box holder further comprises a specimen box inside.

16. The automatic detection instrument for stool specimen according to claim 15, wherein the stirring and blending device comprises a stirring motor and a rotatable sampling spoon;
    the sampling spoon is positioned in the specimen box; when the first lifting frame descends, the sample adding needle is inserted into the specimen box, and the stirring motor is connected with the sampling spoon coaxially.

17. The automatic detection instrument for stool specimen according to claim 1, further comprising a display which is connected with the automatic controller.

* * * * *